US008257975B2

(12) United States Patent
Knapton et al.

(10) Patent No.: US 8,257,975 B2
(45) Date of Patent: Sep. 4, 2012

(54) MARKER DYES FOR PETROLEUM PRODUCTS

(75) Inventors: Daniel J. Knapton, Willowick, OH (US); John S. Manka, Chardon, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 62 days.

(21) Appl. No.: 12/933,455

(22) PCT Filed: Mar. 19, 2009

(86) PCT No.: PCT/US2009/037603
§ 371 (c)(1),
(2), (4) Date: Sep. 20, 2010

(87) PCT Pub. No.: WO2009/120563
PCT Pub. Date: Oct. 1, 2009

(65) Prior Publication Data
US 2011/0020940 A1    Jan. 27, 2011

Related U.S. Application Data

(60) Provisional application No. 61/039,173, filed on Mar. 25, 2008.

(51) Int. Cl.
*G01N 33/26* (2006.01)
*G01N 21/77* (2006.01)
(52) U.S. Cl. ......... 436/60; 436/56; 436/106; 436/164; 436/166; 436/169; 422/420

(58) Field of Classification Search ............. 436/56, 436/60, 100, 106, 140, 164, 166, 169, 180; 422/400, 408, 411, 419, 420, 430, 82.05
See application file for complete search history.

(56) References Cited

U.S. PATENT DOCUMENTS

| | | | | |
|---|---|---|---|---|
| 4,735,631 A | * | 4/1988 | Orelup | 44/428 |
| 5,145,573 A | | 9/1992 | Riedel et al. | |
| 5,156,653 A | * | 10/1992 | Friswell et al. | 44/328 |
| 5,182,372 A | * | 1/1993 | Derber et al. | 534/857 |
| 5,487,770 A | | 1/1996 | Dyllick-Brenzinger et al. | |
| 5,490,872 A | * | 2/1996 | Friswell et al. | 44/328 |
| 5,672,182 A | | 9/1997 | Smith et al. | |
| 6,002,056 A | * | 12/1999 | Smith et al. | 585/3 |
| 6,514,917 B1 | | 2/2003 | Smith et al. | |
| 2005/0227369 A1 | | 10/2005 | Richardson et al. | |
| 2008/0206874 A1 | * | 8/2008 | Manka | 436/2 |

FOREIGN PATENT DOCUMENTS

| | | |
|---|---|---|
| WO | 2003078551 | 9/2003 |
| WO | 2007014903 | 2/2007 |
| WO | 2008106337 | 9/2008 |

OTHER PUBLICATIONS

Written Opinion from corresponding PCT Application No. PCT/US2009/037603 completed Jun. 18, 2009.

* cited by examiner

*Primary Examiner* — Maureen Wallenhorst
(74) *Attorney, Agent, or Firm* — Christopher D. Hilker; David M. Shold

(57) ABSTRACT

The present invention relates to using a marker in a functional fluid, which survives the use of the functional fluid in an application, with a reagent solution to identify the functional fluid rapidly either before, during or after the functional fluid's use and which is a suitable method for identifying a functional fluid in the field, and which may employ the use of test wipe, or medium, that contains the reagent solution.

9 Claims, No Drawings

MARKER DYES FOR PETROLEUM PRODUCTS

FIELD OF THE INVENTION

The present invention relates to the determination of the identity of functional fluids. In particular, the invention relates to using a marker in a functional fluid that can survive the service conditions of the functional fluid and provide a means for identifying the fluid before, during and after the fluid's use. The present invention also relates to a system for identifying a functional fluid that includes a marker in the functional fluid and a reagent, that when contacted with the marked fluid, results in a visible change that allows for the identification of the fluid.

BACKGROUND OF THE INVENTION

Functional fluids are employed in a variety of automotive, off-highway vehicles, on-highway vehicles, equipment, machines, metal working and industrial applications. It is important to know the identity of such functional fluids to prevent the improper utilization or unauthorized counterfeiting of the functional fluid. A proper functional fluid helps to insure the good condition of the device and/or equipment containing the functional fluid and may also impact warranty agreements. It is, therefore, desirable to be able to determine the identity of such functional fluids.

Methods exist for the analysis and identification of functional fluids using various reagents in determining the presence and/or concentration of various constituents of the functional fluids. Specific reagents may be employed for determining the presence and concentration of components in functional fluids. These methods generally analyze for pH, coloring agents, and contaminants using reactive reagents on test strips. These methods also generally require controlled conditions for the reactive reagents to function properly. Further, these methods may be subjective and inaccurate.

Markers have been used to identify fluids. Proton accepting chemical substances, that at a solution concentration of below about 50 milligrams per liter, impart little or no significant color to organic solvents, have been proposed as markers, or taggants, especially for petroleum-derived fuels. The marker is dissolved in a liquid to be identified, and then subsequently detected by performing a chemical test on the marked liquid. Markers are sometimes employed by government agencies to ensure that the appropriate tax has been paid on particular grades of fuel. Oil companies also mark their products to help assist in identifying diluted or altered products. These companies often go to great expense to make sure their branded petroleum products meet certain specifications, for example, volatility and octane number, as well as to provide their petroleum products with effective additive packages containing detergents and other components. Consumers rely upon product names and quality designations to assure that the product being purchased is the quality desired. Thus, it is important to be able to identify a marker in a petroleum product.

Traditionally, the presence of a marker substance is detected and optionally quantified by extracting the fuel with an aqueous or significantly aqueous solution of an acid substance, the precise nature of which can be varied according to the characteristics of the marker substance. The acid reacts with the basic marker compound to produce a readily visible, more or less intensely colored cation that is dissolved in the aqueous acid phase. This method is disclosed in U.S. Pat. No. 5,145,573. Additionally, a method has been disclosed in WO 03/078551 A2 where the acidic substance has been applied to a test strip. The test strip is dipped into the oil and a diazo-type marker reacts with the acidic substance in the test strip and changes color.

The quantity of marker substance in the extract may also be measured, for instance, by visible light absorption spectrophotometry, the results of which are then compared with a reference standard to determine the original concentration of basic marker in the fluid. It may be necessary to make repeated, typically two or three, extractions of the fluid to recover the entire amount of marker originally present in order for complete quantification. Additionally, the extracted, separated phase is classifiable as a hazardous waste and presents problems of safe and lawful disposal, especially when examinations are made "in the field." Furthermore, the functional fluid which was tested may be contaminated by such processes, making its return to its original source undesirable, presenting additional waste disposal problems.

It would be desirable to have an accurate and easy analytical method to determine the identity of a functional fluid. It would further be desirable to have an accurate analytical method to determine the identity of the functional fluid in the field. The present invention rapidly indicates the identity of a functional fluid, including lubricating oils, 4 stroke engine oils, 2 stroke engine oils, automatic and manual transmission fluids, continuously variable transmission fluids, infinitely variable transmission fluids, greases, gear oils, hydraulic fluids, metalworking fluids, antifreeze fluids, coating system fluids, cooling systems fluids, farm tractor fluids, transformer fluids, fuels such as diesel, gasoline, biofuels, emulsified fuels, and the like in the field.

Many owners and/or operators of equipment that depend on these functional fluids currently depend on off-site labs to determine the specific identify of a fluid when such questions arise, such as in warranty resolutions. A tool that would allow identification of a functional fluid in the field would speed warranty resolution and similar issues. Additionally, various absorbent materials (wipes, shop towels, paper towels, and napkins) are normally used in checking functional fluids. The present invention does not require the use of absorbent materials as the functional fluid can be used on any surface type material as long as the surface does not chemically interfere with the marker and reagent.

Many markers currently used in functional fluid for the purpose of identification cannot be utilized once the functional fluid has been used in an application and/or subjected to its service conditions. The applications involved, which may subject the functional fluid to high or low temperatures, high or low pressure, physical stress, various other conditions and combination thereof, often break-down or otherwise affect marker compounds. These markers do not survive the use of the functional fluid in the applications involved, limiting their ability to allow for the identification of such functional fluids. The present invention provides markers that survive the applications of the functional fluid and allow for rapid and accurate identification of a functional fluid in the field, before, after or during its use in such applications.

A need exists for a simple and rapid method of chemically analyzing a sample of a fluid on a qualitative basis to determine origin or other useful property before, during or after the use of the fluid in its intended application. The present invention will rapidly indicate the identity of a functional fluid such as lubricating oils, engine oil, 4 stroke and 2 stroke engine oils, automatic and manual transmission fluids, continuously variable transmission fluids, infinitely variable transmission fluids, greases, gear oils, hydraulic fluids, metalworking fluids, antifreeze fluids, coating system fluids, cooling systems fluids, farm tractor fluids, transformer fluids, fuels such as diesel, gasoline, biofuels, emulsified fuels, and the like in the field.

It is an object of this invention to provide an easy and convenient delivery system to accurately analyze the identity of a functional fluid. It is a further object of the invention to provide a method to analyze functional fluids rapidly in the field. It is still a further object of the invention to provide a delivery method such as an aerosol, mist, spray, wet wipe, liquid or semi liquid for a stable reagent that can identify a marker in a functional fluid which thus identifies the functional fluid. It is still the object of the present invention to provide a method to test the identity of a functional fluid in the field rapidly by untrained personnel and without precision measurement. It is still a further object of the invention to provide a diagnostic kit for identification of functional fluids rapidly in the field.

SUMMARY OF THE INVENTION

The present invention is a method to determine the identity of a functional fluid comprising:
(1) adding a marker component to a functional fluid;
(2) using the marked functional fluid in an application, wherein the marker component survives the service conditions of the fluid;
(3) obtaining a sample of the marked functional fluid before, during or after the fluid's use in the application;
(4) placing the sample of functional fluid and a reagent solution on a test medium such that they are in contact with each other;
(5) reacting the marker in the functional fluid sample on the test medium with the reagent solution to produce a visible change;
(6) analyzing the results of the reaction by determining or comparing the resultant visible change; and
(7) determining the identity of the functional fluid.

The invention further provides a diagnostic kit for the analysis of marker containing functional fluids comprising a medium, a liquid, a semi liquid, an aerosol or mist containing a reagent solution comprising a mineral acid, an organic acid, an organic base, a mineral base, an oxidizing agent, a reducing agent, a chelating agent, metal salts, or combinations thereof; and a method to determine the identity of the fluid comprising instruction, pictures, drawings, photographs, and combinations thereof.

DETAILED DESCRIPTION OF THE INVENTION

The present invention provides a method and device such as a kit for analyzing and monitoring the identity of functional fluids. The functional fluids come from innumerable sources, including internal combustion engines, stationary engines, turbines, transmissions, differentials, pumps, metalworking operations, cooling systems, industrial systems and the like. The functional fluids include automatic transmission fluids, continuously variable transmission fluids, infinitely variable transmission fluids, traction drive transmission fluids, manual transmission fluids, power steering fluids, antifreeze fluids, lubricating oils, greases, crankcase lubricants, cylinder lubricants, mineral oils, Group 1, 2, 3 or 4 base oils, differential lubricants, turbine lubricants, gear lubricants, gear box lubricants, axle lubricants, farm tractor fluids, transformer fluids, compressor fluids, cooling system fluids, metal working fluids, hydraulic fluids, brake fluids, industrial fluids, fuels, infinitely variable transmission fluid, and the like. In one embodiment, the functional fluid is an automatic transmission fluid. In one embodiment, the functional fluid is a power steering fluid. In one embodiment, the functional fluid is an internal combustion fuel such as gasoline and/or diesel. In one embodiment, the functional fluid is compressor fluids such as air compressor lubricants and/or turbine lubricants. In one embodiment, the functional fluid is an internal combustion engine oil. In one embodiment the functional fluid is tested after some time in use, up to and including the fluid's service life.

The Reagents

The choice of reagent used to identify the functional fluid depends on the type of functional fluid being tested and the marker present in the fluid. Reagents for the purposes of this invention are substances that enable the verification of the presence of the surviving marker in the functional fluid. The reagents function by a variety of mechanisms in how the indicator responds. The reagents function by reacting with the marker compound and resulting in a color change as seen through visual examination, colorimetry, photometry, fluorescence, chemiluminescence, combinations thereof, and the like.

The color the reagent gives upon testing can be selected, depending on the type of functional fluid being tested and/or the level of degradation of the functional fluid, by controlling the combinations of reagents and marker compounds used. Certain colors contrast strongly to the usual color of the functional fluid which is preferred. The choice of a suitable color may be determined by a particular application. For example, in one embodiment automatic transmission fluid for passenger cars is colored red for identification purposes. It would be inappropriate to use a reagent and marker combination that gives a red response to indicate a positive identification result in an automatic transmission fluid. For example, in an automatic transmission fluid, a selection of the color indication is in the range of varying blues to greens and mixtures thereof would be more desirable.

The reagents of the present invention act as a developing agents, in that the reagent makes conspicuous the presence or absence of a marker substance in a functional fluid. Developing agents include mineral or organic acids, organic or mineral bases or basic substances, oxidizing agents, reducing agents, chelating agents and the like. Combinations of developing agents may be used.

In one embodiment the reagent is an acid. Examples of acids include perchloric acid, hydroiodic acid, hydrobromic acid, hydrochloric acid, sulfuric acid, nitric acid, chloric acid, bromic acid, perbromic acid, iodic acid, and periodic acid, fluoroantimonic acid, magic acid $FSO_3HSBF_5$, carborane superacid $H(CHB_{11}Cl_{11})$, fluorosulfuric acid $FSO_3H$, triflic acid $CF_3SO_3H$, phosphoric acid, carboxylic acids, phenol, aromatic acids and the like. This can also include acidic buffer solutions. The acids can be used alone or in combination.

In one embodiment, the reagent is a base. Examples of bases include potassium hydroxide, barium hydroxide, cesium hydroxide, sodium hydroxide, strontium hydroxide, calcium hydroxide, lithium hydroxide, rubidium hydroxide, butyl lithium, lithium diisopropylamide, sodium amide, sodium hydride, sodium carbonate, potassium carbonate, magnesium carbonate, ammonium carbonate, ammonia, magnesium hydroxide, calcium oxide, magnesium oxide, lithium oxide, hydrates of the hydroxides, amine bases such as: alanine, methylamine, pyridine and the like. This can also include basic buffer solutions. The bases can be used alone or in combination.

The concentrations at which the reagents are used are not overly limited. It is understood that some concentrations of reagents will provide faster and/or more accurate results than others and that these optimum concentrations may vary between specific reagents and mixtures of reagents. In one embodiment the reagent is a 3.0 M, 1.5 M, or 0.6 M hydrochloric acid. In another embodiment the reagent is 0.6M, 1.0 M or 2.0 M potassium hydroxide.

Optionally, in preparing the reagents, stabilizers may be added. The stabilizers include inhibitors such as para-amino benzoic acid, phenyl alpha-napthyl amines and the like. Another class of stabilizers includes acids such as hydrochloric acid, dithiophosphoric acid, phosphoric acid, thio-phosphoric acids. Another class of stabilizers includes bases such as sodium hydroxide, sodium bicarbonate, potassium hydroxide, and the like. Another class of stabilizers includes buffer solutions which are most commonly aqueous solutions of a weak acid and its conjugate base or a weak base and its conjugate acid, to maintain the pH of the reagents as necessary. The stabilizers can be used alone or in combination. In one embodiment, the stabilizer is employed in the range 1 equivalent to or greater than the amount of reagent being reduced.

Each type of reagent can be used alone or in combinations as the reagent of the present invention. Further, the reagents/indicators may be a combination of reagents or one reagent. Each type of reagent may be used in a reagent solution, comprising one or more reagents and one or more solvents, in the range of about 0.001 wt. % to about 5 wt. %, and in another embodiment in the range of about 0.05 wt. % to about 2 wt. %, and in another embodiment in the range of about 0.1 wt. % to about 1 wt %, wherein the percent by weights are with respect to the reagent solution.

Solvents

Suitable solvents may be used with the reagents, forming a reagent solution. The solvent used depends on the type of functional fluid being tested, the delivery system being used and the indicator being used. Combinations of solvents are also useful when the reagent, depending on the application and type of analysis desired, is not soluble in the functional fluid. Particularly, solvents or combinations of solvents which present a desirable combination of properties including good solvency power and miscibility with the functional fluid and the reagent, low vapor pressure at ambient temperatures, high flash points and the like.

Solvents include aliphatic, unsaturated and aromatic hydrocarbons, alcohols, glycols, glycol ethers, lower alcohols, such as methanol, ethanol and propanol, ethers, esters, amides, amines, water and the like. Combinations of solvents may be used.

In one embodiment, the reagent solution is a mixture of an inorganic acid, a carboxylic acid and a solvent. When used as the reagent solution, such a mixture can improve the marker response, help clean and/or keep clean the test medium, the sample of functional fluid itself, or combinations thereof, leading to more efficient testing. In one embodiment the solvent is isopropyl alcohol, the inorganic acid is hydrochloric acid, and the carboxylic acid is 2-ethylhexanoic acid.

In some embodiment the reagent solution used contains a reagent, and one or more solvents. In some embodiments, the reagent solution comprises hydrochloric acid, isopropanol and 2-ethylhexanoic acid. The solution may be a mixture of about equal parts of hydrochloric acid, isopropanol and 2-ethylhexanoic acid. The solution may also be mixture of equal parts of hydrochloric acid and 2-ethylhexanoic acid with the balance made up of isopropanol. In one embodiment the mixture is 10 to 100% wt hydrochloric acid, 0 to 50% wt 2-ethylhexanoic acid and 0 to 40% wt isopropanol. In another embodiment the mixture is 20 to 60% wt hydrochloric acid, 10 to 60% wt 2-ethylhexanoic acid and 10 to 40% wt isopropanol. Additional solvents and/or reagents may be added to these mixtures to prepare the reagent solution.

It is understood that the term reagent when used in the application, unless otherwise indicated, can mean either the reagent compound or compounds themselves with no added solvent or the reagent solution comprising a mixture of the reagent compound or compounds and one or more solvents. The solvent is present in the reagent solution in the range of about 1 wt. % to about 99.99 wt. %, in one embodiment about 5 wt. % to about 98 wt. % and in another embodiment about 1 wt. % to about 95.5 wt. % of the reagent solution.

The Markers

The marker substance is chosen to be compatible with, or not adverse to, the functional fluid. In one embodiment, the marker is chosen to survive the application and/or service conditions the functional fluid is exposed to during its use. In general, a marker substance is used to identify new functional fluids. In some cases however, it is useful to validate the identity of a used functional fluid for, as an example, warranty claims. In this case the marker needs to survive and be detectable after experiencing the typical operating conditions of the functional fluid. In the case of markers, the marker may be added prior to the functional fluid being used so that the "lock and key" marker-reagent system is available to use under the present invention. This additization can be done at the lubricant manufacturer's production facility or at any time prior to performing the "lock and key" method of this invention.

Further, "lock and key" type markers are also included as reagents in this invention. The "lock and key" type markers include where a "lock", a material soluble in the fluid, which may or may not be stable to the conditions of use depending on the desired time to test for the lock, is added to the functional fluid and a marker, or "key", is chosen to specifically detect the lock. This may also take the form where a determined functional additive, present in the functional fluid for performance reasons, is targeted and a "key" marker is selected to indicate the presence of the "lock".

Markers may be used alone or in combination with one another. Where multiple markers are used, the mixture may still be referred to as a marker substance, in the singular.

Marker substances include diazo dyes, anthraquinone dyes, phthalein dyes, and the like, metals, metal salts, metal oxides, metal coordination complexes and the like or other substances compatible with the lubricant. In one embodiment the marker substance is stable to, and survives, the service conditions of the fluid. The marker substances of the present invention may be used to identify either new or used functional fluids. Combinations of these substances may be used.

In one embodiment of the present invention, the marker compound has a formula represented by the following formula:

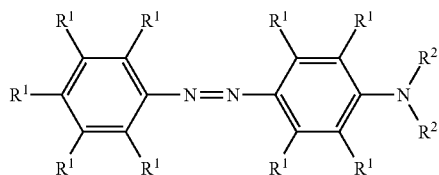

wherein each $R^1$ is independently hydrogen, a —COOH group, a halide, a Nitro group, a cyano group, an azo group, a sulfonic acid group, a phosphoric acid group, amino group, alkoxy group, an ester group, an amide group, a trifluoromethyl group, a phenyl group, or an alkyl group; and wherein each $R^2$ is independently hydrogen, an alkyl group or any other hydrocarbyl group. In one embodiment the alkyl groups of $R^1$ and $R^2$ contain from 1 to 10, 1 to 5, or 1 to 3 carbon atoms.

In another embodiment of the present invention, the marker compound comprises 4-dimethylaminoazobenzene, 4-diethylaminoazo-benzene, p-dimethylaminoazobenzene-o-carboxylic acid, 2-aminoazo-toluene; thymol blue; thymolphthalein; malachite green carbinol base or mixtures thereof.

The amount of marker present in the functional fluid is not overly limited as long as there is enough marker to effectively react with the reagent and there is not so much marker that it interferes with the performance of the functional fluid. The markers may be present in the functional fluid at concentrations of 10 to 10,000 ppm or 10 to 1,000 ppm. In another embodiment the makers are present in the functional fluid at 20 to 500 ppm; 25 to 350 ppm, 30 to 130 ppm; or 30 to 100 ppm.

The marker may be added to the functional fluid by itself or with other materials in the form of a concentrate. Concentrates are well known in the field functional fluids, particularly lubricants as a means of packaging and delivering additives and other components to base lubricants and other fluids. In one embodiment, the concentrate is a mixture of the marker compound and a solvent. This solvent is not particularly limited and includes those solvents discussed above. In one embodiment the solvent is an alcohol and in another embodiment the alcohol contains 4 to 20 carbon atoms. In another embodiment the alcohol contains 5 to 15 carbon atoms and in yet another embodiment 8 to 10 carbon atoms, e.g. Conden Liniol 810.

The marker compound itself may be soluble in water, substantially soluble in water, substantially insoluble in water or insoluble in water. In one embodiment the present invention requires a reaction to occur between the marker compound and the reagent in order for the indicative effect to occur and be observable. In these embodiments, the present invention does not require nor rely on a water extraction of the marker compound from the functional fluid and in some embodiments, excludes such a water extraction.

In another embodiment, the marker compound is added to the functional fluid in the form of a concentrate where the concentrate is a mixture of the marker compound and a polymeric compound. This polymeric compound may be one or more conventional additives well known in the art. In one embodiment the polymeric compounds that may be in the concentrate include dispersants, detergents, antiwear agents, friction modifiers, metal deactivators, corrosion inhibitors, seal swell agents, viscosity modifiers, pour point depressants, thickeners, and antioxidants, either alone or in combinations with one another.

Test Substrate or Medium

The functional fluid to be tested is placed upon any surface or medium. This surface or medium includes absorbent material, nonabsorbent material and combinations thereof. The medium includes paper, cellulosic material such as cellulose, cellulose nitrate, cellulose acetate, cellulosic material, wood, paper, chromatography paper, filter paper, polymeric fibers, natural fibers, finely woven fabrics, metal, glass, glass micro fiber, sintered glass, silica and/or alumina coated surfaces such as thin layer chromatography plates, plastic, plastic laminated material, composites, cotton (such as shop rags), cloth, and combinations thereof. Other absorptive/adsorptive materials, having the, general physical properties and characteristics of chromatography paper are also acceptable. The medium must be capable of receiving a sample of the functional fluid but is not necessarily absorbent. The medium should be compatible with the specific indicator and/or developing agent; that is, in one embodiment it should not promote oxidation or acid-base reactions.

In one embodiment the preferred medium includes "Whatman" white colored chromatography paper or filter paper in the form of an easy to dispense and use wipe. In one embodiment, absorptive paper, such as chromatography paper is preferred, in particular for lubricating oil samples. Light colored chromatography paper provides a consistent background which contrasts well with the functional fluid, provides for a more conspicuous color change and has the proper adsorptive affinity for the various components of an oil. For example, in one embodiment, the coloration of the indicator may become more pronounced over time on the outer edges of the sample spot on the paper as the indicator colored portion of the mixture is swept along with the mobile phase (oil and solvent) faster than the darker components of the used oil, such as sludge. This is due to the differences in adsorptive affinity for the paper. This difference in affinity becomes important as the concentration of sludge in the oil sample increases over the service life. In another embodiment, the reagent solution carries the soot and/or sludge away from the point of addition, leaving a clear and circular space where any dot formed by a positive identification result is clearly visible.

It is to be understood that depending on the type of functional fluid being analyzed and the particular functional purpose of the fluid, for instance, whether for gasoline powered engines as opposed to diesel powered engines, the test medium may need to be varied, whether the medium is chromatography paper or other type of paper, polymeric fiber material or nonabsorbent material like glass, plastic or metal. The medium may differ in its adsorptive affinity for the various components in the particular fluid, porosity, density, wicking ability, or other physical characteristics such as color.

Light colored media provides a consistent background which contrasts well with most functional fluids, and provides for a more conspicuous color change and has the proper adsorptive affinity for the various components of the functional fluid. In one embodiment the medium includes "Whatman" white colored chromatography paper or filter paper in the form of an easy to dispense and use wipe.

The medium may differ in its adsorptive affinity for the various components in the particular functional fluid, such as porosity, density, wicking ability, or other physical characteristics such as color.

The shape of the medium is unimportant, so long as it is of an effective size to permit dispersion of the functional fluid sample, but small enough to be economical and limit waste.

The reagent may be applied to the medium either before or after the sample of functional fluid. In one embodiment the test medium can be a wipe, or other medium, that is treated with the reagent solution and then packaged and/or kept ready for testing, and then the sample of functional fluid is added to the test medium. In another embodiment, the sample of functional fluid may be added to the test medium and then the reagent is added.

Optional Components

Optional components may be added to the reagent solutions or the functional fluids. These include surfactants to help media wetting, maskants and fragrances to improve customer appeal, antifoam additives to improve product manufacture and use, acids and bases to adjust the pH of the indicator solutions and buffers to maintain the pH of the indicator solutions. The optional components can be used alone or in combination.

Examples of surfactants include ionic, anionic (based on sulfate, sulfonate or carboxylate anions), sodium dodecyl sulfate (sds), ammonium lauryl sulfate, and other alkyl sulfate salts, sodium laureth sulfate, also known as sodium lauryl ether sulfate (sles), alkyl benzene sulfonate, soaps, or fatty acid salts, cationic (based on quaternary ammonium cations), cetyl trimethylammonium bromide (ctab) a.k.a. hexadecyl trimethyl ammonium bromide, and other alkyltrimethylammonium salts, cetylpyridinium chloride (cpc), polyethoxylated tallow amine (poea), benzalkonium chloride (bac), benzethonium chloride (bzt), zwitterionic (amphoteric), dodecyl betaine, dodecyl dimethylamine oxide, cocamidopropyl betaine, coco ampho glycinate, nonionic, alkyl poly(ethylene oxide), alkyl polyglucosides, including: octyl glucoside, decyl maltoside, fatty alcohols, cetyl alcohol, oleyl alcohol, cocamide MEA, cocamide DEA, cocamide TEA, NEODOL™ 25, fatty alcohols, ethoxylated alcohols, alkyl polyglucosides, TRITON™ bg-10 surfactant, TRITON™ CG-110 surfactant, branched secondary alcohol ethoxylates, TERGITOL™ TMN series, ethylene oxide/propylene oxide copolymers, TERGITOL™ L series, TERGITOL™ XD, XH, and XJ surfactants, TRITON™ CF surfactants, TRITON™ DF surfactants, TERGITOL™ minfoam surfactants, nonylphenol ethoxylates, TERGITOL™ NP series, octylphenol ethoxylates, TRITON™ X series, secondary alcohol ethoxylates, TERGITOL™ 15-S series, TRITON™ Ca surfactant, TRITON™ N-57 surfactant, TRITON™ X-207 surfactant, surfynol surfactants, primary amines, tertiary amines, monoalkyl and polyamines, ethoxylated amines, ethoxylated diamines, propoxylated amines, amine salts, quaternary ammonium salts, ethoxylated quaternary salts, propoxylated quaternary salts, amine oxides, amides, ethoxylated amides, esters: nonionic surfactants: ethoxylated fatty acids, amphoteric compounds, sulfosuccinates and sulfosuccinimates, fatty acid esters, fatty alcohols, alkanolamides, alkyl and alkyl ether sulfates, lauryl sulfates and lauryl ether sulfates, alkyl aryl sulfonates and alpha olefin sulfonates, alkoxylated nonionic surfactants, soya lecithins, alkyl sulfates, alkyl ether sulfates, imidazolines, alkanolamides, DOWFAX™ anionic surfactants, DuPont sulfonates, zonyl fluorosurfactants, peg esters and glyceryl esters, sorbitan esters/sorbitan ester ethoxylates, silicone surfactants, naphthalene condensates, sodium alkylnaphthalene sulfonates, pegol block copolymers, alkyl pyrrolidones, alkyl and glycol esters, emerest and trydet ethoxylated fatty acids and polyethylene glycol fatty acid esters, pilot hydrotropes, aristonate petroleum sulfonates, aristol sulfonatable oils, amido-amines, betaine amphoterics imidazolines imidazolinium amphoterics sulfosuccinates, fatty acid diethanolamides, neodol alcohols and the like. The surfactants can be used alone or in combination.

Examples of maskants and fragrances include Abbarome™ 011, Acalea TT, allyl amyl glycolate, ambrettolide, amyl cinnamic aldehyde, amyl salicylate, andrane, anethole 21/22, anethole usp, aphermate, apo patchone, Bacdanol™, benzyl butyrate, benzyl propionate, benzyl salicylate, bicyclononalactone, Bornafix™, canthoxal, Cashmeran™, Cassiffix™, Cedramber™, cedrenyl acetate, celestolide, cinnamalva, citral dimethyl acetal, intarome cotton odorsynthesis, intarome lavender musk odorsynthesis, citronalva, citronellol 700 jax, citronellol 750, citronellol 950, citronellol coeur, citronellyl acetate a, citronellyl acetate coeur, citronellyl acetate pure, citronellyl formate, clarycet, clonal, coniferan, cyclabute, Cyclacet™, Cyclaprop™, cyclemone A, cyclobutanate, Cyclogalbaniff™, cyclohexyl ethyl acetate, cyclohexyl ethyl alcohol, damascol 4, decyl methyl ether, delta damascone, dihydro cyclacet, dihydro floralate, dihydro floralol, dihydro myrcenyl acetate, dihydro terpineol, dihydro terpinyl acetate, dihydro terpinyl acetate dsa, dimethyl benzyl carbinol, dimethyl benzyl carbinyl acetate, dimethyl benzyl carbinyl butyrate, dimethyl cyclormol, dimethyl octanol, dimethyl phenyl ethyl carbinyl acetate, dimyrcetol, diola, dipentene 5100, Dulcinyl™ recrystallized, ethyl ortho methoxy benzoate, ethyl phenyl glycidate, fleuramone, fleuranil, floralate, floralol, floraloz-one, fraistone, fructone, Galaxolide™ 50 BB, Galaxolide™ 50 DEP, Galaxolide™ 50 DPG, Galaxolide™ 50 IPM, galbanum coeur, gelsone, geraldehyde, geraniol 5020, geraniol 7030, geraniol 980 pure, geraniol coeur, geranyl acetate A, geranyl acetate extra, geranyl acetate pure, grisalva, Helional™, herbac, hexalon, hexenyl salicylate, cis-3, hexyl acetate, hexyl cinnamic aldehyde, hexyl salicylate, hyacinth body, hyacinth body no. 3, hydratropic aldehyde dimethyl acetal, hydroxyol, hypo-lem, indolarome, indolene 50, intreleven aldehyde, intreleven aldehyde special, ionone 100%, ionone alpha, ionone alpha beta regular, ionone beta, iso amyl butyrate, iso amyl salicylate, iso bornyl propionate, iso butyl quinoline, iso cyclemone E, iso cyclo citral, iso cyclo geraniol, Iso E Super™, isoproxen, jasmal, jasmelia, Jessemal™, Kharismal™, Koavone™, Kohinool™, lavonax, lemsyn, Liffarome™, Lindenol™, Lyral™, lyrame, lyrame super, maritima, Meijiff™, melafleur, methyl cedryl ketone chinese, methyl cinnamic aldehyde alpha, methyl ionone gamma a, methyl ionone gamma coeur, methyl ionone gamma pure, methyl lavender ketone, Montaverdi™, muguesia, muguet aldehyde, muguet aldehyde 50 bb50, myrac aldehyde, myrcenol super, myrcenyl acetate, neoproxen, nerol 800, nerol 850, nerol 900, neryl acetate jax, ocimene, ocimenyl acetate, octacetal, orange flower ether, orivone, Orriniff™ 25% ipm, oxaspirane, ozofleur, Pamplefleur™, peomosa, Phenafleur™, Phenoxanol™, phenoxyethyl iso butyrate, phenoxyethyl propionate, phenyl ethyl acetate, phenyl ethyl alcohol, phenyl ethyl benzoate, phenyl ethyl formate, phenyl ethyl iso butyrate, phenyl ethyl salicylate, piconia, precyclemone B, prenyl acetate, proflora, pseudo linalyl acetate, reseda body, rosalva, rosamusk, roseate, rosemarel, salicynalva, sanjinol, Santaliff™, spirodecane, Strawberiff™, styralyl propionate, syvertal, terpineol 900, terpineol alpha jax, terpineol extra, terpinolene 20, terpinolene 90, terpinolene 90 pq, terpinyl acetate extra, terpinyl acetate jax, Tetrahydro Muguol™, Tetrahydro Muguol™ coeur, tetrahydro myrcenol, tetrameran, tobacarol, Triplal™, Unipine™ 60, Unipine™ 85, Vandor™ B, vanoris, verdol, Verdox™, Verdox™ HC, verdural b extra, verdural extra, Vertenex™, Vertenex™ HC, Vertofix™ coeur, vertoliff, vigoflor, violiff, and mixtures thereof. also included in maskants are additives that act as odor scavengers such as amine scavengers and hydrogen sulfide scavengers like epoxides, basic amines, and the like. The maskants and fragrances can be used alone or in combination.

Examples of antifoams/defoamers are polysiloxanes, polyacrylates, esters, insoluble oils, mineral oils, surfactants, amorphous silica, silicone emulsions, and the like. The antifoams/defoamers can be used alone or in combination.

Examples of acids and bases are given above. These materials also include acidic or basic buffer solutions. The acids can be used alone or in combination, as can the bases. Examples of aqueous buffers include combinations of ammonium chloride and ammonia, formic acid and sodium formate, acetic acid and sodium acetate, and the like. The aqueous buffers can be used alone or in combination.

The optional component is used in the range of about 0% to about 20% wt, in one embodiment about 0.01% to about 5% wt, and in another embodiment about 0.1% to about 2% wt of the reagent solution.

Propellants

The reagent solution can be sprayed onto the test media with a pump type sprayer or can be sprayed from an aerosol can. The propellant used must be compatible with the reagents. In one embodiment, the propellant is oxygen free or substantially free of oxygen. For example, with redox indicators the propellant should be oxygen free and chemically/ oxidatively inert. Inert propellants include nitrogen, hydrocarbons, propane and butane, chlorofluorocarbons (CFCs), hydrocarbons, propane, n-butane and isobutene, dimethyl ether (DME) and methylethyl ether, nitrous oxide, hydrofluoroalkanes (HFA), HFA 134a (1,1,1,2-tetrafluorethane), HFA 227 (1,1,1,2,3,3,3-heptafluoropropane), saturated light hydrocarbons, $C_3$-$C_6$ (e.g., propane, isobutane, n-butane), CFC-11, HCFC-22, HCFC-142b, dimethyl ether CFC-11, HCFC-22, HCFC-142b, HCFC-152a, HFC-125, CFC-11, HCFC-22, HCFC-142b, HFC-227 ea, CFC-11, CFC-12, CFC-114, HCFC-22, HCFC-142b, compressed gases (carbon dioxide, air, nitrogen, nitrous oxide), SF6, fluorinated dimethyl ethers, Bis(difluoromethyl)ether, vinyl chloride monomer, and mixtures thereof. In one embodiment the propellant is free of halogens. Combinations of propellants may be used.

Liquids/Semi Liquids

In a liquid or semi liquid delivery system, the reagent solution is in a liquid or semi liquid form. Generally, a liquid is a form of matter intermediate between gases and solids, in which the molecules are much more highly concentrated than gases, but much less than solids. Generally a semi liquid is a material that has an increased viscosity over a liquid substance. Generally, this increased viscosity is the result of the addition of materials that increase viscosity such as viscosity modifiers, polymers, tackifiers, clays, fillers, thickeners, rheology modifiers and the like. Semi liquids include gels, emulsions, suspensions, dispersions, additized liquids and the like. The container is any container capable of dispensing the liquid or semi liquid. The dispensing systems place the reagent solution onto the sample or in another embodiment the medium with the sample onto the reagent solution. Dispensing systems for liquids and/or semi liquids include droppers, squeeze containers, pour containers, pipettes, pumps without propellants, sprays without propellants, rollers, brushes, dipping and the like.

Visual Indicia

Analysis of the reacted test sample can be accomplished by visual inspection of the reacted test sample using a provided visual indicia as a guide. Analysis occurs after an effective period of time to allow for the reaction between the components of the functional fluid and the reagents. Generally the time for reaction is in the range of about immediate or about 0.01 seconds to about 1 hour, in another embodiment about 30 seconds to about 30 minutes, in another embodiment about 1 minute to about 15 minutes, and in another embodiment about 1 minute to about 5 minutes. In the embodiment, the time for the reaction is immediate.

The visual indicia may include an artistic rendering, a reproduction of a photograph of one or more functional fluids in various conditions with and without the reagent. The visual indicia generally include one representation, two representations or more than two representations of one or more functional fluids disposed upon the same, similar or different test media in various conditions with and without the reagent. In one embodiment the preferred visual indicia is one or more representations showing a positive identification result and one or more representations showing a negative identification result. A descriptive text corresponding to each of these examples may be provided.

In one embodiment the visual indicia depicted is dispersed upon the same or similar medium provided in the kit, to assure that the kit user compares the sample to be tested to examples produced under similar conditions. It is to be understood that a different number of indicia may be provided.

Method

The present invention is a method to determine the identity of a functional fluid comprising: (1) adding a marker component to a functional fluid; (2) using the marked functional fluid in an application, wherein the marker component survives the service conditions of the fluid; (3) obtaining a sample of the marked functional fluid before, during or after the fluid's use in the application; (4) placing the sample of functional fluid and a reagent solution on a test medium such that they are in contact with each other; (5) reacting the marker in the functional fluid sample on the test medium with the reagent solution to produce a visible change; (6) analyzing the results of the reaction by determining or comparing the resultant visible change; and (7) determining the identity of the functional fluid.

In one embodiment, the sample of functional fluid is applied to the test medium and then the reagent solution is applied to the test medium, allowing the two to react on the test medium. In another embodiment, the reagent solution is applied to the test medium first, and in some embodiments is integrated into the test medium and/or applied some time in advance of the rest of the steps being carried out. Then the sample of functional fluid is added to the test medium, allowing for the reaction to occur. In yet another embodiment, the sample of functional fluid and reagent solution may be added simultaneously or multiple additions of either may be made in any order. In yet other embodiments, either or both the functional fluid and/or reagent solution may be applied to the test medium by one or more of the various methods discussed herein, including the use of droppers, dipping cans, and wet wipes.

It is not necessary that the sample be taken during actual operation of the engine or other equipment or machinery in order to obtain a representative sample of the functional fluid. The sample of functional fluid may be taken at any time before, during and/or after operation of the engine or equipment. The functional fluid sample can be new, used or combinations thereof. In one embodiment the functional fluid test is especially useful during and/or after operation for some period of time.

The diagnostic kit contains a means to apply the reagent solution and/or the functional fluid, which may include a dropper, pipette, squeeze container, pour container, brush, pumps, vapor chamber, dipper container, a wet wipe, an aerosol can (which includes the actuator, valve, and optionally an agitator ball) or spray pump that can be sealed containing the reagent solution comprising a base indicator, an acid indicator, a metal indicator, a marker indicator and mixtures thereof and further includes written instructions and/or a set of visual indicia depicting samples of the functional fluid disposed upon a medium printed in color on the package with descriptive text. In one embodiment, the diagnostic kit includes the media upon which the functional fluid sample is placed for testing. In one embodiment, the test medium of the kit includes a wet wipe wherein the wipe contains the reagent solution. In one embodiment, the visual indicia shows a depiction of a functional fluid with a positive identification result (i.e. light color, etc) and also a functional fluid with a negative identification result (i.e. dark color and/or different color, etc).

In one embodiment the present invention excludes identification by observing a compound removed from the function fluid by a water extraction. A water extraction occurs where a compound, such as a dye, in a functional fluid is removed from the functional fluid and drawn into an aqueous solution, due to the compound's miscibility in water and the observance of the compound, without any reaction taking place, in the water solution is the only indicator provided.

In one embodiment the functional fluid is an engine oil. The engine oil sample, or other functional fluid to be tested, under ordinary circumstances may be obtained using a dipstick provided as a part of the engine, transmission or other equipment under lubrication. The user will withdraw an amount of oil along with the dipstick or other device, which may then be wiped on the test medium or the oil which will collect into a drop at the end of the dip stick may then placed upon the test medium. Typically, less that 1 milliliter of oil is necessary for the analysis. Once the oil test sample has been placed on the test medium, the sample spot may be sprayed with the reagent solution or the reagent solution may otherwise be applied to the test medium and the marker immediately begins to react. In another embodiment the test medium may be a wipe that has been pretreated with the reagent solution and which may be used to remove the oil, or other functional fluid, from the dipstick, or other piece of equipment, resulting in the contact of the marked functional fluid with the reagent solution. The user allows for an effective period of time to allow for the reaction between the marker components of the fluid and the reagent. Next, the user determines whether or not a color change occurred, and refers to the visual indicia as a guide. The user may consult the descriptive text accompanying the example selected to determine the condition or identity of the functional fluid.

The marking/identification of a functional fluid, for instance an automatic transmission fluid or automotive engine oil, is desirable because counterfeiting and adulteration/dilution of genuine functional fluids is a large concern of fluid suppliers as counterfeiting and adulteration results in a loss of profits, customer durability problems with vehicles, customer warranty claims, etc. due to a lack of adequate lubricant performance. A simple, easy to use marker system is beneficial since different functional fluids are usually indistinguishable visually. Chemical analyses or physical properties can tell various functional fluids apart but these analyses require expensive laboratory test equipment and often take too long to be a practical end user identification test. The disclosed "lock" and "key" technology enables an end user to exclude a counterfeit or adulterated product based on a color change resultant from the reaction between a known "lock" added to a functional fluid to yield a "marked" fluid and a "key" reagent present in the aerosol or spray which reacts with the "lock" reagent to give a predictable color change upon contact.

SPECIFIC EMBODIMENT

Unless otherwise indicated, the marked fluids prepared in the examples below are indicated as follows: (a) a paper test strip is wetted with the specified reagent solution; (b) a drop of the marked fluid is added to the wetted portion of the paper test strip; (c) upon exposure of the marked fluid to the wetted portion of the paper test strip, a red, blue or purple dot, depending on the marker and reagent solution used, is observed indicating a positive identification of the fluid.

Example 1

A marked passenger car engine oil is prepared as follows: (1) a 1.3 wt % solution of methyl yellow indicator is prepared in Conden Liniol 810, a mixture of C8-10 alcohols. The mixture of methyl yellow and alcohol is heated to 100° C. until the solution is homogeneous; (2) to 1 quart of a premium conventional 10W-30 passenger car engine oil 11.4 g of the marker solution prepared in step (1) is added. The marked engine oil is then diluted with untreated 10W-30 passenger car engine oil to 5 quarts total volume 10W-30 premium conventional passenger car engine oil, full synthetic passenger car engine oil or semi-synthetic passenger car engine oil. This results in the marker solution being present in the finished fluid at 0.3 wt %.

The marked passenger car engine oil prepared above is indicated with an aqueous solution of 3 M HCl resulting in a red dot indicating a positive identification of the fluid.

Example 2

A marked passenger car engine oil is prepared according to the procedure of Example 1 above. The marked passenger car engine oil prepared is indicated with a mixture of 3 M HCl, isopropanol and 2-ethylhexanoic acid, resulting in a red dot indicating a positive identification of the fluid.

Example 3

A marked passenger car engine oil is prepared as follows: (1) a 0.05 wt % blend of methyl yellow indicator in an olefin copolymer viscosity modifier is prepared. The mixture of methyl yellow and viscosity modifier is heated at 100° C. for 5 hours then blended at 500 rpm stirring for 30 minutes at 70° C.; (2) 312 grams of the marked viscosity modifier is mixed into 3688 g of a 5W-30 synthetic passenger car engine oil prepared without viscosity modifier. The marked viscosity modifier in the finished fluid is 7.8 wt %.

The marked passenger car engine oil prepared above is indicated with an aqueous solution of 3 M HCl, resulting in a red dot indicating a positive identification of the fluid.

Example 4

A marked passenger car engine oil is prepared according to the procedure in Example 3. The marked passenger car engine oil prepared above is indicated with a mixture of 3 M HCl, isopropanol and 2-ethylhexanoic acid, resulting in a red dot indicating a positive identification of the fluid.

Example 5

A marked diesel engine oil is prepared as follows: (1) A 1.3 wt % solution of methyl yellow indicator is prepared in Conden Liniol 810. The mixture of methyl yellow and alcohol is heated to 100° C. until the solution is homogeneous. (2) 11.4 g of the marker solution is added to 1 quart of a 5W-30 premium conventional diesel engine oil. The marked engine oil is then diluted to 5 quarts total volume 5W-30 premium conventional diesel engine oil. The marker solution in the finished fluid is 0.3 wt %.

The marked diesel engine oil prepared above is indicated with a mixture of 3 M HCl, isopropanol and 2-ethylhexanoic acid, resulting in a red dot indicating a positive identification of the fluid.

Example 6

A marked diesel engine oil is prepared according to the procedure in Example 5. The marked diesel engine oil prepared above is indicated with 3 M HCl, resulting in a red dot indicating a positive identification of the fluid.

Example 7

A marked automatic transmission fluid is prepared as follows: (1) A 1.3 wt % solution of thymolphthalein indicator is prepared in Conden Liniol 810. The mixture of thymolphthalein and alcohol is heated to 100° C. until the solution is homogeneous. (2) 0.25 g of the marker solution is added to 99.75 g of MS9602 automatic transmission. The marker solution in the finished fluid is 0.25 wt %.

The marked automatic transmission fluid prepared above is indicated with 0.066 M KOH, resulting in a purple dot indicating a positive identification of the fluid.

Example 8

A marked automotive gear oil is prepared as follows: (1) A 1.3 wt % solution of methyl yellow indicator is prepared in Conden Liniol 810. The mixture of methyl yellow and alcohol is heated to 100° C. until the solution is homogeneous. (2) 0.16 g of the marker solution is added to 99.84 g of a conventional automotive gear oil. The marker solution in the finished fluid is 0.16 wt %.

The marked automotive gear oil prepared above is indicated with 0.6 M HCl, resulting in a red dot indicating a positive identification of the fluid.

Example 9

A marked passenger car fuel is prepared as follows: (1) a 1.3 wt % solution of thymolphthalein indicator is prepared in Conden Liniol 810. The mixture of thymolphthalein and alcohol is heated to 100° C. until the solution is homogeneous. (2) 0.05 g of the marker solution is added to 99.95 g of BP 87 octane passenger car fuel. The marker solution in the finished fluid is 0.05 wt %.

The marked passenger car fuel prepared above is indicated as follows: (a) a paper test strip is dipped into the marked fuel; (b) 0.06 M KOH is sprayed onto the dipped portion of the paper test strip; (c) upon exposure of the marked passenger car fuel to the spray of KOH, the dipped portion of the paper test strip turns blue indicating a positive identification of the fluid.

Example 10

A marked diesel fuel is prepared as follows: (1) A 1.3 wt % solution of thymolphthalein indicator is prepared in Conden Liniol 810. The mixture of thymolphthalein and alcohol is heated to 100° C. until the solution is homogeneous. (2) 0.05 g of the marker solution is added to 99.95 g of USLD #2 Diesel fuel. The marker solution in the finished fluid is 0.05 wt %.

The marked passenger car diesel fuel prepared above is indicated according to the procedure in Example 9, with 0.066 M KOH, resulting in the strip turning blue indicating a positive identification of the fluid.

Example 11

A marked biodiesel fuel is prepared as follows: (1) A 1.3 wt % solution of thymolphthalein indicator is prepared in Conden Liniol 810. The mixture of thymolphthalein and alcohol is heated to 100° C. until the solution is homogeneous. (2) 0.1 g of the marker solution is added to 99.9 g of rapeseed methyl ester. The marker solution in the finished fluid is 0.1 wt %.

The marked biodiesel fuel prepared above is indicated according to the procedure in Example 9, with 0.066 M KOH, resulting in the strip turning blue indicating a positive identification of the fluid.

Example 12

A marked hydraulic fluid is prepared as follows: (1) A 1.3 wt % solution of thymolphthalein indicator is prepared in Conden Liniol 810. The mixture of thymolphthalein and alcohol is heated to 100° C. until the solution is homogeneous. (2) 0.1 g of the marker solution is added to 99.9 g of hydraulic fluid. The marker solution in the finished fluid is 0.1 wt %.

The marked hydraulic fluid prepared above is indicated with 0.066 M KOH, resulting in a blue dot indicating a positive identification of the fluid.

Example 13

A marked passenger car engine oil is prepared as follows: (1) a 1.0 wt % solution of 4-diethylaminoazobenzene indicator is prepared in Conden Liniol 810. The mixture of 4-diethylaminoazobenzene and alcohol is heated to 100° C. until the solution is homogeneous; (2) 15.2 g of the marker solution is added to 1 quart of a premium conventional 10W-30 passenger car engine. The marked engine oil is then diluted with untreated 10W-30 passenger car engine oil to 5 quarts total volume 10W-30 premium conventional passenger car engine oil, full synthetic passenger car engine oil or semi-synthetic passenger car engine oil. This results in the marker solution being present in the finished fluid at 0.4 wt %.

The marked passenger car engine oil prepared above is then indicated with an aqueous solution of 3 M HCl or with a mixture of 3 M HCl, isopropanol and 2-ethylhexanoic acid, resulting in a red dot indicating a positive identification of the fluid.

Comparative Example 1

A marked passenger car engine oil is prepared as follows: (1) A 1.3 wt % solution of 2-aminoazotoluene indicator is prepared in Conden Liniol 810. The mixture of 2-aminoazotoluene and alcohol is heated to 100° C. until the solution is homogeneous; (2) 19 g of the marker solution is added to 1 quart of a premium conventional 10W-30 passenger car engine. The marked engine oil is then diluted to 5 quarts total volume 10W-30 premium conventional passenger car engine oil, full synthetic passenger car engine oil or semi-synthetic passenger car engine oil. The marker solution in the finished fluid is 0.5 wt %.

The marked passenger car engine oil prepared above is then indicated with an aqueous solution of 3 M HCl, and then also separately indicated with a mixture of 3 M HCl, isopropanol and 2-ethylhexanoic acid, resulting, in both case, in an orange dot indicating a positive identification of the fluid.

Comparative Example 2

A marked passenger car engine oil is prepared as follows: (1) A 2.0 wt % solution of thymol blue indicator is prepared in Conden Liniol 810. The mixture of thymol blue and alcohol is heated to 100° C. until the solution is homogeneous. (2) 11.5 g of the marker solution is added to 1 quart of a premium conventional 10W-30 passenger car engine oil. The marked engine oil is then diluted to 5 quarts total volume 10W-30 premium conventional passenger car engine oil, full synthetic passenger car engine oil or semi-synthetic passenger car engine oil. The marker solution in the finished fluid is 0.3 wt %.

The marked passenger car engine oil prepared above is then indicated with an aqueous solution of 0.066 M KOH, resulting in a blue dot indicating a positive identification of the fluid.

Durability of the Marker System in Gasoline Powered Vehicles

The following engine tests were conducted with various vehicles where the engine oil was changed and the marked engine oil was added to the engine. The vehicle was then run under its normal operating conditions and periodic samples of the marked engine oil were taken and tested to see of the marker still gave a positive result.

Test 1.

Drain samples were taken at various intervals from the engine of a 1999 Dodge Caravan that contained the marked full synthetic passenger car engine oil prepared according to the procedure in Example 1. The used fluid samples were then indicated according to the procedure in Examples 1 and 2. The results are in Table 1 below.

TABLE 1

| Mileage on Engine oil | Paper Test Strip Color |
| --- | --- |
| 508 | Red |
| 1020 | Red |
| 1800 | Red |
| 2000 | Red |
| 3286 | Red |
| 5289 | Red |

The marked engine oil responded positively up to 5289 miles at which point the test was concluded and the engine oil was changed. The application, in this case use of the marked engine oil in a 1999 Dodge Caravan engine, did not affect and/or inhibit the performance of the marker, allowing the marked fluid to be identified even after over 5000 miles of use.

Test 2.

Drain samples were taken at various intervals from the engine of a 1993 Cadillac Sedan Deville that contained the marked full synthetic passenger car engine oil prepared according to the procedure in Example 3. The used fluid samples were then indicated according to the procedure in Example 4. The results are in Table 2 below.

TABLE 2

| Mileage on Engine oil | Paper Test Strip Color |
| --- | --- |
| 750 | Red |
| 1500 | Red |

The marked engine oil responded positively up to 1500 miles and was still pending at the time this application was filed. The application, in this case use of the marked engine oil in a 1993 Cadillac Sedan Deville engine, did not affect and/or inhibit the performance of the marker, allowing the marked fluid to be identified even after 150 miles of use.

Test 3.

Drain samples were taken at various intervals from the engine of a 1999 Dodge Caravan that contained the marked full synthetic passenger car engine oil prepared according to the procedure in Example 13. The used fluid samples were then indicated according to the procedure in Example 13. The results are in Table 3 below.

TABLE 3

| Mileage on Engine oil | Paper Test Strip Color |
| --- | --- |
| 5 | Red |
| 528 | Red |
| 1789 | Red |
| 2021 | Red |
| 3100 | Red |

The marked engine oil responded positively up to 3100 miles at which point the test was concluded and the engine oil was changed. The application, in this case use of the marked engine oil in a 1999 Dodge Caravan engine, did not affect and/or inhibit the performance of the marker, allowing the marked fluid to be identified after 3000 miles of use.

Test 4.

Drain samples were taken at various intervals from the engine of a 2001 Chrysler Sebring that contained a marked conventional passenger car engine oil prepared as in Comparative Example 1. The marked engine oil failed to respond after 27 miles showing the comparative marker fluid did not survive the application after less than 27 miles of use.

Test 5.

Drain samples were taken at various intervals from the engine of a 1993 Pontiac Grand AM that contained a marked conventional passenger car engine oil prepared as in Comparative Example 2. The marked engine oil failed to respond after 5 miles showing the comparative marker fluid did not survive the application after less than 5 miles of use.

Durability of the Marker System in Diesel Powered Vehicles

The following diesel engine test was conducted under the same conditions as the gasoline powered vehicle tests described above.

Test 6.

Drain samples were taken at various intervals from the engine of a 2006 Jeep Liberty that contained the marked diesel passenger car engine oil prepared according to the procedure in Example 5. The used fluid samples were then indicated according to the procedure in Example 5. The results are in Table 6 below.

TABLE 6

| Mileage on Engine oil | Paper Test Strip Color |
| --- | --- |
| 57 | Red |
| 520 | Red |
| 1079 | Red |
| 1535 | Red |
| 2000 | Red |
| 2573 | Red |
| 3011 | Red |

The marked engine oil responded positively up to 3011 miles at which point the test was concluded and the engine oil was changed. The application, in this case use of the marked diesel engine oil in a 2006 Jeep Liberty engine, did not affect and/or inhibit the performance of the marker, allowing the marked fluid to be identified even after over 3000 miles of use.

While the invention has been explained, it is to be understood that various modifications thereof will become apparent to those skilled in the art upon reading the specification. Therefore, it is to be understood that the invention disclosed herein is intended to cover such modifications as fall within the scope of the appended claims.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word about.

Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. Unless otherwise indicated, all percentage values are percents by weight. It is to be understood that the upper and lower amounts, ranges, and ratio limits set forth herein may be independently combined. Similarly, the ranges and amounts for each element of the invention can be used together with ranges or amounts for any of the other elements. As used herein, the expression "consisting essentially of" permits the inclusion of substances that do not materially affect the basic and novel characteristics of the composition under consideration.

What is claimed is:

1. A method to determine the identity of a functional fluid comprising:
    (1) adding a marker component to a functional fluid;
    (2) using the marked functional fluid in an application, where the application has a set of service conditions, and where the fluid used in the application is exposed to the service conditions, and wherein the marker component survives the service conditions of the application;
    (3) obtaining a sample of the marked functional fluid before, during or after the fluid's use in the application;
    (4) placing the sample of functional fluid and a reagent solution on a test medium such that they are in contact with each other;
    (5) reacting the marker in the functional fluid sample on the test medium with the reagent solution to produce a visible change;
    (6) analyzing the results of the reaction by determining the resultant visible change; and
    (7) determining the identity of the functional fluid based upon analysis of the results;
    wherein the sample of the marked functional fluid and the reagent solution are placed on the test medium in any order; wherein the reagent solution comprises a mineral acid, an organic acid, an organic base, a mineral base, an oxidizing agent, a reducing agent, a chelating agent, a metal salt, or combinations thereof;
    wherein the reagent solution and sample of functional fluid are placed onto the test medium using a dropper, pipette, squeeze container, pour container, pump without propellant, spray, roller, brushes, dipping container or mixtures thereof;
    wherein the marker component comprises a marker compound represented by the following formula:

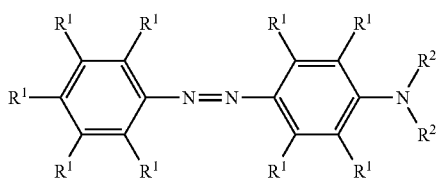

wherein each $R^1$ is independently hydrogen, or a —COOH group; and wherein each $R^2$ is independently hydrogen, or an alkyl group wherein any alkyl groups present independently contain from 1 to 5 carbon atoms.

2. The method of claim 1 wherein the functional fluid is selected from the group consisting of automatic transmission fluids, engine oils, traction drive transmission fluids, manual transmission fluids, power steering fluids, antifreeze fluids, lubricating oils, greases, crankcase lubricants, mineral oils, oils with Group 1, 2, 3 or 4 base oils, vegetable oils, differential lubricants, turbine lubricants, gear lubricants, gear box lubricants, axle lubricants, brake fluids, farm tractor fluids, transformer fluids, compressor fluids, cooling system fluids, metal working fluids, hydraulic fluids, industrial fluids, passenger car fuels, diesel engine fuels, bio-based fuels, continuously variable transmission fluid, infinitely variable transmission fluids, and mixtures thereof;
    wherein the marker component is added to the functional fluid before or during the fluid's use in the application and wherein the marker is selected to survive the fluid's use in the application.

3. The method of claim 1 wherein the marker component is added to the functional fluid in the form of a concentrate comprising the marker compound and a solvent; wherein the marker compound is miscible in the solvent and the solvent is miscible in the functional fluid, and wherein the marker compound is substantially immiscible in water.

4. The method of claim 1 wherein the marker component further comprises 4-dimethylaminoazobenzene, 4-diethylaminoazobenzene, p-dimethylaminoazobenzene-o-carboxylic acid, 2-aminoazotoluene; thymol blue; thymolphthalein, malachite green carbinol base, or mixtures thereof; and
    wherein the reagent solution is selected from one of the following: (a) a reagent solution comprising hydrochloric acid; (b) a reagent solution comprising potassium hydroxide; (c) a reagent solution comprising a mixture of hydrochloric acid, isopropanol and 2-ethylhexanoic acid; and
    wherein the reagent solution is from about 0.001 wt. % to 5 wt. %; and wherein the marker compound is present in the functional fluid from about 10 to 1000 ppm.

5. The method of claim 1 wherein the medium is compatible with the reagent solution and the medium comprises paper, cellulosic material, chromatography paper, filter paper, polymeric fibers, natural fibers, fabrics, polypropylene woven fabric, nonwoven fabric, metal, glass, plastic, composite materials, and combinations thereof; and
    wherein the analysis occurs after an effective period to allow for the reaction between the marker in the functional fluid and the reagent solution.

6. The method of claim 1 wherein determining the identity of the functional fluid is selected from the group consisting of visually comparing the sample against a set of comparative visual indicia depicting the functional fluid and at least one different fluid as a guide, using printed instructions as a guide, comparing photographs depicting at least one different fluid, and combinations thereof.

7. The method of claim 1 wherein the test medium comprises a substrate containing the reagent solution and wherein the reaction between the marked functional fluid and the reagent takes place when the sample of the marked functional fluid is placed on the test medium.

8. The method of claim 1 wherein the functional fluid is exposed to heat, physical stress, or combinations thereof during its use in the application.

9. The method of claim 1 wherein the application of the functional fluid is in an internal combustion engine and wherein the functional fluid is an engine oil.

* * * * *